US00PP12083P2

(12) United States Plant Patent
Zaiger et al.

(10) Patent No.: US PP12,083 P2
(45) Date of Patent: Sep. 11, 2001

(54) PEACH TREE 'SWEET ALICE'

(76) Inventors: Chris Floyd Zaiger, 929 Grimes Ave.; Leith Marie Gardner, 1207 Grimes Ave.; Gary Neil Zaiger, 1907 Elm Ave.; Grant Gene Zaiger, 4005 California Ave., all of Modesto, CA (US) 95358

( * ) Notice: Subject to any disclaimer, the term of this patent is extended or adjusted under 35 U.S.C. 154(b) by 0 days.

(21) Appl. No.: 09/236,779

(22) Filed: Jan. 25, 1999

(51) Int. Cl.[7] ..... A01H 5/00

(52) U.S. Cl. ..... Plt./197

(58) Field of Search ..... Plt./197

*Primary Examiner*—Bruce R. Campell
*Assistant Examiner*—Anne Marie Grünberg

(57) ABSTRACT

A new and distinct variety of peach tree (*Prunus persica*); the features of the tree and its fruit are characterized with the tree budded on Nemaguard rootstock (unpatented), grown on Hanford sandy loam soil with Storie Index rating 95, in USDA Hardiness Zone 9, near Modesto, Calif., using standard commercial cultural fruit growing practices, such as, pruning, thinning, spraying, irrigation and fertilization. Its novelty consist of the following unique combination of features that are desirable in a new variety:

1. Heavy and regular production of fruit.
2. Vigorous and upright growth.
3. Fruit having a high degree of attractive red skin color.
4. Fruit with a mild, sweet, sub-acid taste with very good flavor and eating quality.
5. Fruit with firm flesh, having good storage and shipping quality.
6. Fruit holding firm 7 to 10 days after maturity (shipping ripe).
7. Early maturity of medium to large, yellow flesh, clingstone fruit.

1 Drawing Sheet

ORIGIN OF THE VARIETY

The present new and distinct variety of peach tree (*Prunus persica*) was originated by us in our experimental orchard located near Modesto, Calif., as a seedling from an open pollinated selection of a cross between two selected seedlings with field identification numbers 3HB192 and 104LB628. The heritage of 3HB192 is as follows: 'May Crest Peach' (U.S. Plant Pat. No. 4,064) was crossed with 'Sweet Gem Peach' (U.S. Plant Pat. No. 7,952), resulting in an unnamed selected seedling. This unnamed selected seedling was crossed with 'Tasty Gold Nectarine', producing 3HB192 as progeny.

The cultivar 3HB192 was crossed with 104LB628, resulting in an unnamed seedling. This unnamed seedling was open pollinated, producing the peach tree 'Sweet Alice' as progeny.

The heritage of 104LB628 is as follows: 'May Grand Nectarine' (U.S. Plant Pat. No. 2,794) was open pollinated, resulting in an unnamed seedling. This unnamed seedling was crossed with 'May Crest Peach' (U.S. Plant Pat. No. 4,064), producing 104LB628 as progeny.

'Sweet Alice' was chosen from a large group of sibling seedlings growing on their own root which were planted and maintained under close observation by us. We recognized the desirable fruit characteristics of one seedling, which is the present variety, and selected it for asexual propagation and commercialization.

ASEXUAL REPRODUCTION OF THE VARIETY

Asexual reproduction of the new and distinct variety of peach tree was by budding to Nemaguard rootstock (unpatented), as performed by us in our experimental orchard located near Modesto, Calif., and shows that reproductions run true to the original tree and all characteristics of the tree and fruit are established and transmitted through succeeding asexual propagations.

SUMMARY OF THE VARIETY

The herein new and distinct variety of peach tree is of large size, vigorous, upright growth and a productive and regular bearer of medium to large size, firm, yellow flesh, clingstone fruit with very good flavor and eating quality. The fruit is further characterized by having a high degree of attractive red skin color, holding firm on the tree 7 to 10 days after maturity (shipping ripe), and having good storage and shipping quality. The fruit of the present variety, when compared to the sub-acid Sweet Gem Peach (U.S. Plant Pat. No. 7,952), is similar in flavor and eating quality and is approximately 20 days earlier in maturity.

PHOTOGRAPH OF THE VARIETY

The accompanying color photogaphic illustration shows typical specimens of the foliage and fruit of the present new peach variety. The illustration shows the upper and lower surface of the leaves, an exterior and sectional view of a fruit divided in its suture plant to show flesh color, pit cavity and the stone remaining in place. The photographic illustration of the fruit was taken shortly after being picked (shipping ripe) and the colors are as nearly true as is reasonably possible in a color representation of this type.

DESCRIPTION OF THE VARIETY

The following is a detailed botanical description of the new variety of peach tree, its flowers, foliage and fruit, as based on observations of specimens grown near Modesto, Calif., with color terminology (except those in common terms) in accordance with Reinhold Color Atlas by A. Kornerup and J. H. Wanscher.

Tree:

*Size.*—Large. Pruned 12 to 14 feet in height and 12 to 14 feet in width, primarily for economical harvesting of fruit.

*Vigor.*—Vigorous. Grows to a height of 6 to 7 feet the first growing season. Pruned to 3 to 4½ feet in height the first dormant season when selecting primary scaffolds.

*Form.*—Usually pruned to vase shape.

*Productivity.*—Productive. Normal fruit set is 1½ to more times the amount of desired fruit. Thinning and spacing of fruit is necessary for optimum marketable fruit size.

*Bearer.*—Regular. Amount of fruit set varies with climatic conditions at bloom time.

*Density.*—Medium dense. Pruning to open the center of the tree by removing some of the smaller branches is necessary for sunlight penetration.

*Growth.*—Upright. Normal upright growth with a tendency to spread when tree starts producing a heavy crop load.

*Hardiness.*—Hardiness tested only in USDA Zone 9. Winter chilling requirement estimated to be 700 to 900 hours below 45° F.

Trunk:

*Size.*—Large. Average circumference of 24 inches at 14 inches above the ground on a 10 year old tree. Varies with soil type, climatic conditions and cultural practices.

*Texture.*—Medium shaggy. As the tree grows older, small areas of bark project outward creating a rough or shaggy surface.

*Color.*—Brown to soot brown (5-E-3) to (5-F-3).

Branches:

*Size.*—Medium. Circumference averages 11¾ inches at 30 inches above the ground.

*Texture.*—Smooth to medium rough. Roughness increases with age of branch.

*Lenticels.*—Numerous. Average number of 53 in a 4 square inch section. Average length of 5/32 inch. Average width of 5/64 inch. Color varies from brownish red to reddish brown (8-C-8) to (8-E-8).

*Color.*—Light brown to brown (5-D-5) to (5-E-6).

Leaves:

*Size.*—Large. Average length 6 inches. Average width 1⅝ inches.

*Form.*—Lanceolate, pointed.

*Margin.*—Crenate.

*Thickness.*—Medium.

*Surface.*—Smooth.

*Petiole.*—Medium length ½ inch. Medium thicknesss 3/64 inch. Color — grayish green to deep green (29-C-6) to (30-D-8). Grooved longitudinally.

*Glands.*—Reniform. Number varies from 1 to 4. Average number 2. Medium in size, average diameter 3/64 inch. Color — straw yellow to grayish yellow (3-B-4) to (3-C-4). Located on upper portion of petiole and lower base of leaf blade.

*Color.*—Upper surface — green to dark green (29-F5) to (29-F-7). Lower surface — dull green to green (29-E-4) to (29-E-6).

Flower buds:

*Size.*—Large. Average length ½ inch. Average diameter ⅖ inch. 4 days before bloom.

*Form.*—Plump.

*Pubescence.*—Pubescent.

Flowers:

*Size.*—Large, showy. Average diameter 1½ inches. Average length ¾ inch.

*Petals.*—Number — 5. Obovate, with smooth to slightly scalloped edges. Average length ¾ inch. Average width ⅝ inch.

*Sepals.*—Number — 5. Alternately arranged with petals. Average length 11/64 inch. Average width 5/32 inch. Pubescent. Color — From base of sepal, spreading approximately half way up is violet brown (10-E-6) to (10-F-5), fading into wax yellow to olive yellow (3-B-5) to (3-C-5) on upper half and outer edges of sepal.

*Pollen.*—Present, self-fertile.

*Stamens.*—Number varies from 28–35. Average length 7/10 inch. Filament color — white (1-A-1), turning dark pink with age of bloom. Anther color — cardinal red (10-D-8).

*Pistil.*—Usually one. Pubescent. Average length 63/100 inch. Color — yellowish white to pastel yellow (1-A-2) to (1-A-4).

*Aroma.*—None.

*Blooming period.*—Date of First Bloom: Mar. 2, 1997. Date of Last Bloom: Mar. 9, 1997. Varies slightly with climatic conditions.

*Color.*—Pink to light pink (10-A-3) to (10-A-2). Color fades with age of bloom.

Fruit:

*Maturity when described.*—Firm ripe.

*Date of first picking.*—May 20, 1997.

*Date of last picking.*—May 25, 1997. Varies slightly with climatic conditions.

*Size.*—Medium to large. Average diameter axially — 2¼ to 2½ inches. Average transversely in suture plane — 2½ to 2⅝ inches. Average weight 169 grams. Varies with number of fruit per tree, soil type, climatic conditions and cultural practices.

*Form.*—Nearly globose, only slightly elongated in suture plane.

*Suture.*—Shallow, extends from base to apex.

*Ventral surface.*—Rounded, nearly smooth.

*Apex.*—Rounded to slight pistil point.

*Base.*—Retuse.

*Cavity.*—Rounded. Slightly elongated in suture plane. Average depth ½ inch. Average breadth 1 inch.

Flesh:

*Ripens.*—Evenly.

*Texture.*—Firm.

*Fibers.*—Few, small, tender.

*Aroma.*—Slight.

*Amygdalin.*—Undetected.

*Eating quality.*—Very good.

*Flavor.*—Very good.

*Soluble solids.*—Brix 10.1°.

*Juice.*—Moderate amount, mild, sub-acid, sweet.

*Color.*—Butter yellow to maize yellow (4-A-5) to (4-A-6). Pit cavity — grayish yellow to amber yellow (4-B-5) to (4-B-6).

Stem:

*Size.*—Average length ⅜ inch. Average width ⅛ inch, enlarged at point of fruit attachment.

*Color.*—Yellowish green to olive green (1-B-5) to (1-D-4).

Skin:

*Thickness.*—Medium.

*Texture.*—Medium, tenacious to the flesh.

*Down.*—Moderate, medium length.

*Tendency to crack.*—None.

*Color.*—Sunflower yellow to golden yellow (4-A-7) to (4-B-7) ground color, partially overspread with light red to madder red (10-A-7) to (10-B-7), amount of red varies with amount of skin exposed to sunlight.

Stone:

*Type.*—Clingstone.

*Size.*—Large. Average length 1 7/16 inches. Average width 1 1/16 inches. Average thickness 7/8 inch.

*Form.*—Varies from ovate to obovate.

*Base.*—Usually rounded, varies from straight to rounded.

*Apex.*—Very slight point, nearly rounded.

*Surface.*—Furrowed toward apex, pitted throughout, heavier toward base. Both furrows and pits are relatively shallow.

*Sides.*—Equal to unequal, varies with some stones having one side extending further from suture plane with slightly deeper furrows and pits.

*Tendency to split.*—Slight.

*Color.*—Light tan to brownish yellow (5-B-6) to (5-C-7).

Use: Dessert. Market — local and long distance.

Keeping quality: Good. Holds well on the tree after maturity and also in cold storage for 10 days without internal breakdown.

Shipping quality: Good. Minimal flesh bruising and skin scarring in packing and shipping trials.

Disease resistance/susceptibility: No specific testing for relative plant/fruit disease resistance/susceptibility has been designed. Under close observation during planting, growing, and harvesting of fruit, under normal cultural and growing conditions near Modesto, Calif., no particular plant/fruit disease resistance or susceptibility has been observed.

The present new variety of peach tree, its flowers, foliage and fruit herein described may vary in slight detail due to climate, soil conditions and cultural practices under which the variety may be grown. The present description is that of the variety grown under the ecological conditions prevailing near Modesto, Calif.

We claim:

1. A new and distinct variety of peach tree, substantially as illustrated and described, characterized by its large size, vigorous, upright growth and being a productive and regular bearer of medium to large yellow flesh, clingstone fruit; the fruit is further characterized by being nearly globose in shape with a high degree of attractive red skin blush, having a sweet, mild, sub-acid taste with very good flavor and eating quality and, in comparison to the sub-acid peach Sweet Gem (U.S. Plant Pat. No. 7,952), the new variety is 20 days earlier in maturity.

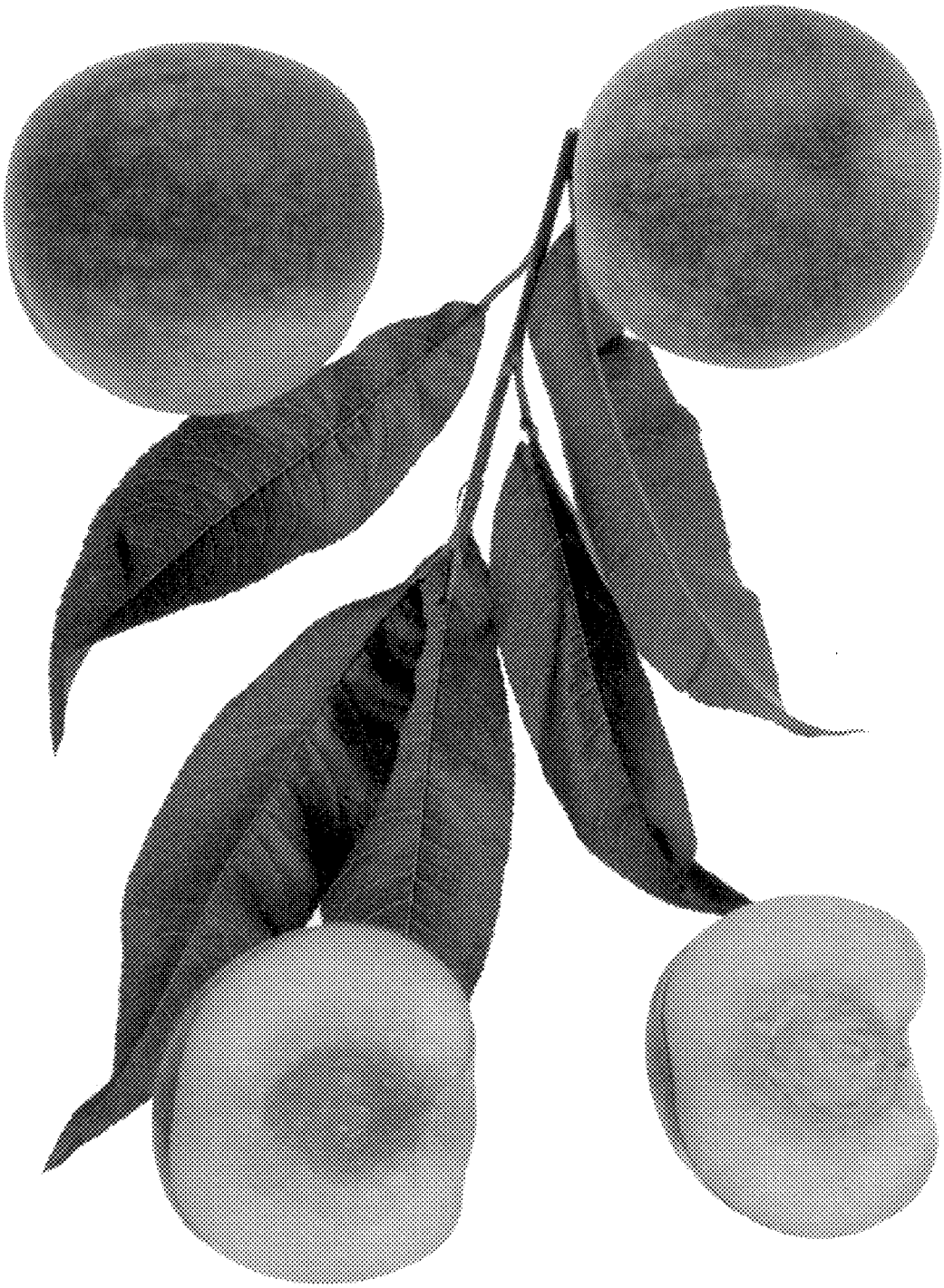

* * * * *